United States Patent [19]

Poignant

[11] 3,969,521

[45] July 13, 1976

[54] PHARMACEUTICAL COMPOSITIONS CONTAINING TETRAHYDROALSTONINE AND METHOD FOR TREATING CIRCULATION DISORDERS

[75] Inventor: Jean-Claude Poignant, Bures-sur-Yvette, France

[73] Assignee: Science Union et Cie, Societe Francaise de Recherche Medical, Suresnes, France

[22] Filed: Oct. 17, 1974

[21] Appl. No.: 515,785

[30] Foreign Application Priority Data

Aug. 18, 1975 Germany .......................... 2439523

[52] U.S. Cl. .............................................. 424/262

[51] Int. Cl.² ...................................... A61K 31/475

[58] Field of Search .................................. 424/262

[56] References Cited

OTHER PUBLICATIONS

Chemical Abstracts 65:4284b (1966).

Chemical Abstracts 75:150147r (1971).

*Primary Examiner*—Jerome D. Goldberg

*Attorney, Agent, or Firm*—Behr & Woodbridge

[57] ABSTRACT

Pharmaceutical compositions containing tetrahydroalstonine or a therapeutically acceptable salt thereof are disclosed. These compositions are useful for treating circulation disorders and more particularly brain circulation disorders.

3 Claims, No Drawings

PHARMACEUTICAL COMPOSITIONS CONTAINING TETRAHYDROALSTONINE AND METHOD FOR TREATING CIRCULATION DISORDERS

DESCRIPTION OF THE PRIOR ART

Tetrahydroalstonine has already been disclosed as an adrenolytic agent in the French Pat. 1.397.537 (to CIBA), indicating some pharamacological properties but without indicating any therapeutical use of these pharmalogical properties.

Moreover, G. H. SVOBODA and co-workers have studied the hypoglycemic properties of this alkaloid in comparison with that of other alkaloids extracted from the genus Vinca (Lloydia 27 (1964) 361).

Further, a thesis has studied the effect of tetrahydroalstonine as well as some non-steroidal anti-inflammatory drugs on blood-sugar levels and carrageenin-induced paw oedema in the rat (Albin B. Kocialski Diss. Abstract Int. B. 1971,31 (12) 7476 - CA 75 (1971) 150 147). The findings have been negative.

SUMMARY OF THE INVENTION

It has been found that tetrahydroalstonine is useful in improving the circulation of blood and the overall metabolic processes of the brain in mammals. It has been found useful in treating vascular disorders involving blood circulation in the brain of elderly subjects. Said subjects include, but are not limited to, domestic animals such as dogs and cats, farm animals such as sheep, cattle, horses, and the like as well as other warm-blooded mammals including also human beings. The compound is particularly useful where the subject is suffering from thromboembolic diseases or cerebal arteriosclerosis.

DETAILED DESCRIPTION OF THE INVENTION

It has now been found that the compound possesses an improving effect of the brain circulation and the brain metabolism and is useful in treating the vascular disorders mainly of the brain ciculation in elderly patients or patients having suffered from thromboembolic diseases or cerebral arteriosclerosis.

The compound is represented by the formula:

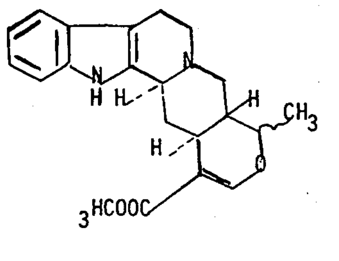

It exists in racemic or optically-active form. As a base, it may be salified with a therapeutically compatible mineral or organic acid such as hydrochloric acid, formic acid, tartaric acid or nicotinic acid.

It is obtained from barks or roots of various genus of Rauwolfia, Alstonia or Vinca as previously described in the literature.

The improving effect on the brain circulation have been demonstrated by several tests in dogs and in rats. The tested compounds have been found more active than Papaverine and Vincamine, compounds which are recognized as drugs improving the brain circulation. Moreover, the compounds of the invention are practically deprived of toxicity. They also exert a favourable effect on the peripheral blood circulation.

Moreover, tetrahydroalstonine and the acid addition salts thereof have been found active on the central nervous system. At low dosages, they are endowed with stimulating properties. At higher dosages, they exert some sedative effects. Tetrahydroalstonine can thus be differentiated from its isomer Raubasine. Raubasine has not this diphasic effect. It is merely endowed with sedative properties.

At high dosages tetrahydroalstonine and the acid addition salts thereof increased the Hexobarbital-induced sleeping time in rodents. They increase the time of inducing the sleep after injection of Nembutal, even at low dosages. Tetrahydroalstonine increases the analgetic effect of Morphine. On the contrary, Raubasine does not exert such effect.

In the therapeutical practice of this invention, tetrahydroalstonine and the acid addition salts thereof may be administered to warm-blooded patients suffering from circulation disorders. More specifically, they may be utilized in human or veterinary medicine for patients suffering from brain circulation disorders such as thromboembolic diseases or cerebral arteriosclerosis. They may also be utilized in human or veterinary medicine for treating patients suffering from peripheral vascular disturbances such as acrocyanosis or chilblain.

The used dosages may range from 0.5 mg/kg to 100 mg/kg of body weight daily depending on the therapeutic use and the age of the patient. The daily dosages are preferably divided in one or several unit dosages in order to insure 1 to 4 administrations daily. They may be used by oral, parenteral or rectal way but the oral way is presently the preferred one.

They have found more particularly benefitful for treating brain circulation disorders in elderly people or intoxicated patients.

Tetrahydroalstonine and its acid addition salts can be formulated for the practice of the invention into various pharmaceutically acceptable dosage forms such as tablets, capsules, pills, coated tablets, sustained release tablets ampuls, phials, suppositories, granules, drinkable or injectable suspensions and the like, by combining the active ingredient with a suitable inert, nontoxic pharmaceutically acceptable carrier or diluent, according to the methods well-known in the art. Such dosage forms may additionally include lubricants, diluents, excipients, binders, fillers, flavoring and sweetening agents and other therapeutically inert ingredients, necessary for the formulation of the desired preparation.

The following examples further illustrate the invention and demonstrate the effectiveness of the claimed methods of treatment.

EXAMPLE 1

Effect of tetrahydroalstonine on the brain blood circulation and on the consumption of oxygen and of glucose by the brain.

This test has been carried out on lots of five dogs weighing from 16 to 20 kg. The dogs have been previously anaesthetized with chloralose by intravenous way and the intravenous injection of 50 mg heparine for each dog is renewed every 150 minutes.

The brain blood flow is determined volumetrically after a catheter has been inserted in both left and right internal maxillary veins toward the superior cerebral veins and ligating the auricular veins. The average arterial blood pressure is determined by dissection of a Table 2 evidences the action of tetrahydroalstonine on the cerebral flow.

TABLE II

EFFECTS OF TETRAHYDROALSTONINE ON THE BRAIN CIRCULATION

| TIME | DC | $PO_2$vc | $O_2$/min. | $O_2$ cap. | art. pH | art. $QO_2$ | arterial Q gluc. in mg | consumption in Gluc./min. | G/O | CE p. 100 glucose | $\frac{\Delta PCO_2}{\Delta QO_2}$ | $\frac{\Delta H^+}{\Delta QO_2}$ | $\Delta QO_2$ |
|---|---|---|---|---|---|---|---|---|---|---|---|---|---|
| 0 | 111,0 | 33,50 | 6,19 | 4,26 | 7,41 | 14,85 | 971 | 8,43 | 1,36 | 7,83 | — 112,01 | −9,68 | +5,58 |
| +45 min. | 90,0 | 28,50 | 6,14 | 5,05 | 7,39 | 14,16 | 900 | 6,66 | 1,08 | 8,22 | — 109,97 | −4,44 | +6,82 |
| +67 min. | 99,0 | 24,25 | 8,40 | 5,95 | 7,425 | 14,50 | 919 | 11,58 | 1,38 | 12,73 | — 114,84 | −6,75 | +8,49 |
| +90 min. | 112,5 | 21,75 | 10,38 | 6,07 | 7,455 | 14,25 | 949 | 12,49 | 1,20 | 11,70 | — 111,05 | −7,96 | +9,23 |
| +112 min. | 112,5 | 23,0 | 9,74 | 5,88 | 7,44 | 13,95 | 972 | 13,39 | 1,37 | 12,24 | — 103,93 | −7,39 | +8,66 |
| +135 min. | 92,0 | 19,75 | 9,22 | 6,33 | 7,48 | 14,18 | 997 | 11,78 | 1,28 | 12,84 | — 129,74 | −8,75 | +10,02 |

DC = Cerebral blood flow in ml/mn
$O_2$cap. = amount of oxygen supplied to the brain tissues
$PO_2$vc = partial pressure of venous oxygen in the brain brachial artery and insertion of a catheter connected with a Statham $P_{23}$Db transducer.

Femoral blood flow was measured with an electromagnetic flowmeter (Statham).

The various parameters have been recorded by means on a polygraph and the hemodynamic survey has been afforded with two tracks-cathodic tubes.

Tetrahydroalstonine has been administrated perorally at a dosis of 100 mg/kg.

On arterial and venous blood sample the concentration of glucose has been determined enzymatically according to the method of hexokinase (C. Hennon and co-workers).

The determination of the pressure of oxygene ($PO_2$) has been carried out with a polarographic analyser and that of carbonic anhydride ($PCO_2$) in the arterial or venous brain blood, using a Duo-Matic electrometer IL 123.

Results

The results have been collected and summarized in table 1.

Tetrahydroalstonine affects significantly the metabolism of the brain. The difference in concentration between arterial and venous oxygen, the consumption of oxygen per minute and the concentration of oxygen in the brain capillars are increased. Therefore, it appears that the amounts of oxygen supplied to the brain tissues are increased. This increase in the consumption of oxygen gives rise to a decrease of the partial pressure in brain venous oxygen ($PO_2$VC). This finding is followed by an increase in the consumption of glucose by the brain. Consequently, the ratio $$\frac{\text{consumed oxygen}}{\text{concentration in oxygen}}$$

does not statistically significantly vary.

For the same reasons, it has been shown in every case an increase in the ratio $$\frac{\Delta PCO_2}{\Delta H^+}$$

TABLE I

EFFECTS OF TETRAHYDROALSTONINE ON THE DOGS'S BLOOD FLOW

| PERIOD OF TIME | CEREBRAL FLOW in ml/mn | CONCENTRATION in oxygen/mn | CONSUMPTION in glucose/mn | $QO_2$ | CONCENTRATION in capillary oxygen | GIO | FEMORAL VEIN FLOW |
|---|---|---|---|---|---|---|---|
| Controls | 116,8 ±4,9 | 9,5 ±1,6 | 6,8 ±1,4 | 8,1 ±1,1 | 5,7 ±0,6 | 0,8 ±0,2 | 22,5 ±1,8 |
| Tested dogs at 45 minutes | 89,8 ±12,5 | 12,8 ±2,5 | 7,1 ±1,6 | 14,3 ±2,1 | 9,3 ±1,3 | 0,6 ±0,1 | 38,0 ±2,3 |
| Tested dogs at 67 minutes | 92,4 ±12,7 | 12,4 ±2,6 | 10,7 ±2,5 | 13,1 ±1,5 | 8,7 ±1,1 | 0,9 ±0,2 | 38,7 ±4,0 |
| Tested dogs at 90 minutes | 95,8 ±15,1 | 12,4 ±2,7 | 11,3 ±1,7 | 12,6 ±1,4 | 8,5 ±1,2 | 1,0 ±0,1 | 37,1 ±1,9 |
| Tested dogs at 112 minutes | 90,6 ±13,9 | 11,5 ±2,4 | 12,1 ±2,7 | 12,4 ±1,5 | 8,4 ±1,1 | 1,1 ±0,2 | 34,5 ±2,1 |
| Tested dogs at 135 minutes | 84,8 ±13,0 | 11,4 ±2,6 | 10,9 ±2,4 | 12,9 ±1,4 | 8,5 ±1,0 | 1,2 ±0,3 | 27,7 ±2,4 |

$$G/O = \frac{\text{CONSUMPTION IN GLUCOSE}}{\text{CONCENTRATION IN OXYGEN}} \text{ per mn}$$

Conclusions

They show the vasodilatatory effect on the blood femoral flow on previously anaesthetized dogs. The vaso dilatory effect is clear and can be observed on all the animal from the 45th minute after oral ingestion to, at least, the 112th minute.

In one case out of five, tetrahydroalstonine has given rise to a noticeable decrease of the blood arterial pressure.

Conclusively, it can be established that tetrahydroalstonine causes a noticeable and extended over a large period of time increase of the blood flow and a significant improvement in the brain metabolism as ascertained by an increase in the consumption of oxygen and glucose in the brain.

EXAMPLE 2

Effects of tetrahydroalstonine on the recovery of learned memories on rats.

Tetrahydroalstonine has been tested on lots of rats in order to determine how fast it allows the recovery of learned memories after supramaximal electroshock in comparision with Vincamine and Papaverine. These last compounds are known to be active on the circulation namely as vasodilating agents.

In this test, as described by C. Giurgea (J. Pharmacol. (Paris) 3 17 (1972)), the rats are submitted to a submaximal electroshock which causes a spatio-temporal desorientation. This syndrom is evidenced by the difficulties the tested animals encountered for crossing over a maze filled with cold water without any error, after they have been submitted to the electroshock. The rats have been previously trained to swimm through this maze and the training has been renewed four times for 2 days.

The electric shock was delivered by means of a Neurovar apparatus (ALVAR Electronics) the third day. 20 Minutes after the electro shock, each lot of rats is tested and the time for crossing over the maze is determined. Immediately after, the rats received the compound to be tested by intra oesophageal tubing. Each lot is then experienced four times, 1, 2, 3, and 4 hours after the electroshock.

The score of performances of each individual is recorded and every error during the crossing over noticed.

The compounds to be tested (papaverine, vincamine and tetrahydroalstonine) are given to the animals, suspended in an aqueous solution of carboxymethylcellulose and sorbitan monooleate.

Papaverine and vincamine were administered at dosis ranging from 1 to 20 mg/kg. Tetrahydroalstonine was administered at a dosis of 0.6 mg/kg, 6 mg/kg and 60 mg/kg.

A lot of rats received only the aqueous solvent under the same volume (0.5 ml/100 g animal) as controls.

RESULTS

The effects on the recovery of learned memories are summarized in Table III and Table IV. Therein are reported for each lot of rats the number of errors and the average time for crossing over the maze during the 5 tests performed after the animals have been subjected to the electroshock.

TABLE III

TEST OF CROSSING OVER AN AQUATIC MAZE AFTER SUPRAMAXIMAL ELECTROSHOCK

| COMPOUNDS TESTED AND DOSIS | Number of animals per lot | EFFECT ON RECOVERY AFTER 20 minutes | | 60 minutes | | 120 minutes | | 180 minutes | | 240 minutes | |
|---|---|---|---|---|---|---|---|---|---|---|---|
| | | T | E | T | E | T | E | T | E | T | E |
| Controls none | 20 | 132,0 | 13,6 | 89,5 | 9,2 | 76,8 | 7,4 | 49,7 | 4,9 | 35,5 | 4,4 |
| Tetrahydroalstonine 0,6 mg/kg P.O. | 20 | 124,2 | 12,3 | 85,2 | 8,4 | 66,4 | 6,2 | 37,9 | 3,1 | 29,4 | 2,0 |
| 6 mg/kg P.O. | 20 | 133,5 | 12,3 | 75,1 | 6,9 | 52,5 | 4,4 | 54,6 | 3,6 | 23,8 | 2,5 |
| 60 mg/kg P.O. | 20 | 135,0 | 10,6 | 62,2 | 5,8 | 28,8 | 2,7 | 18,8 | 1,6 | 20,1 | 1,8 |
| Papaverine 10 mg/kg P.O. | 20 | 154,2 | 14,3 | 75,5 | 7,3 | 54,2 | 4,8 | 49,0 | 4,7 | 25,4 | 2,4 |
| 20 mg/kg P.O. | 20 | 150,7 | 14,0 | 89,8 | 10,4 | 53,4 | 5,6 | 29,7 | 2,9 | 32,8 | 3,0 |
| Vincamine 10 mg/kg P.O. | 20 | 135,6 | 10,8 | 82,7 | 7,2 | 44,1 | 4,6 | 52,8 | 5,6 | 38,6 | 4,3 |
| 20 mg/kg P.O. | 20 | 124,5 | 14,3 | 58,4 | 7,1 | 38,2 | 5,2 | 22,1 | 2,5 | 24,2 | 3,2 |

T = average time for crossing over in seconds
E = average number of errors
The treatment has been given 20 mn after the electroshock, immediately after the first crossing over

TABLE IV

STATISTICAL STUDY OF THE VARIATIONS IN THE NOMBER OF ERRORS

| COMPOUNDS AND DOSIS | Number of animals | | EFFECTS AFTER 20 minutes | 60 minutes | 120 minutes | 180 minutes | 240 minutes |
|---|---|---|---|---|---|---|---|
| PAPAVERINE | 20 | a | + | – | – | – | – |
| 10mg/kg P.O. | | b | NS | NS | NS | NS | 0,0005 |
| PAPAVERINE | 20 | a | + | + | – | – | – |
| 20 mg/kg P.O. | | b | NS | NS | NS | 0,005 | 0,01 |
| VINCAMINE | 20 | a | – | – | – | + | – |
| 10 mg/kg P.O. | | b | NS | NS | NS | NS | NS |
| VINCAMINE | 20 | a | + | – | – | – | – |
| 20 mg/kg P.O. | | b | NS | NS | NS | 0,0005 | 0,025 |
| TETRAHYDROALSTONINE | 20 | a | – | – | – | – | – |
| 0,6 mg/kg P.O. | | b | NS | NS | NS | 0,01 | 0,0005 |
| TETRAHYDROALSTONINE | 20 | a | – | – | – | – | – |
| 6 mg/kg P.O. | | b | NS | NS | 0,05 | 0,05 | 0,005 |
| TETRAHYDROALSTONINE | 20 | a | – | – | – | – | – |
| 60 mg/kg P.O. | | b | NS | 0,025 | 0,005 | 0,0005 | 0,0005 |

a = variation of average figures as regard as the controls
b = statistical value (student's test)
+ worsened score
– improvement These results show that the control animals needed after electroshock a large period of time for recovery. The period for crossing the maze is 3 times longer 20 mn after the electroshock, than for normal rats. It remains twice longer 240 mn after the electroshock for the control animals than for the normal rats. Moreover, 20 minutes after the electroshock the number of mistakes is four times higher than for normal animals.

The review of the figures indicate that control animals recover progressively their memories and that the related performances are improved from a crossing over to the subsequent crossing over. This improvement is of significance between 20 and 60 mn after electroshock, slighter between 1 and 3 hours and very slight between 3 and 4 hours. The more the number of mistakes is already decreased, the weaker is the late recovery.

A few number of control rats still improved their performance at 180 and 240 mn but the differences are not statistically significant.

The animals treated with papaverine showed a delayed improvement in their performance which appeared statistically significant only after 240 mn at 10 mg/kg and after 180 mn at 20 mg/kg.

The animals treated with 10 mg/kg of vincamine did not show any decrease in the number of mistakes. However, a slight improvement in the performances after 2 hours have been noticed.

At a dosis of 20 mg/kg the number of mistakes is significantly decreased 3 and 4 hours after the electroshock. This improving effect initiated 60 mn after the electroshock i.e. 40 minutes after the administration of vincamine.

Tetrahydroalstonine produced an effect which is closely related to the used dosis. The higher is the dosis, the earlier is the statistically significant decrease of the number of mistakes.

This decrease appeared:

after 180 mn at 0.6 mg/kg after 120 mn at 6 mg/kg after 60 mn at 60 mg/kg.

At the dosage of 6 mg/kg the improving effect of tetrahydroalstonine started after 60 mn.

Conclusively it can ascertained that papaverine, vincamine and tetrahydroalstonine have all an improving effect on the recovery of learned memory. Vincamine and more papaverine exert some effect at a dosis of 20 mg/kg but this effect is delayed so that it can not be strictly differentiated from the spontaneous return to the normal state.

Tetrahydroalstonine appears to be more active. A dosis of 0.6 mg/kg competes with that of 20 mg/kg of papaverine or vincamine. At the highest tested dosage the recovery of the memory is complete 120 mn after the convulsive shock.

Toxicology

The search of an acute toxicity has been carried out on lots of mice (Rockland strain) weighing from 18 to 22 mg. The mice received orally increasing dosis of tetrahydroalstonine suspended in an aqueous solvent.

The animals are kept under survey for 7 days and the deaths are recorded. The average lethal dosis has been graphically calculated according to the method of Wilcoxon and Litchfield. A lot of mice received only the solvent as controls. The average lethal dosis has been found far superior to 3 g/kg.

The compound is practically devoid of toxic effect.

Effects on the Central Nervous System

Tetrahydroalstonine exerts on the central nervous system effects which differentiates its action from this of raubasine. Tetrahydroalstonine has a slight stimulating action at low dosages and a sedative effect at higher dosages (from 20 to 40 mg/kg per os). On the contrary, raubasine is merely a sedative at dosis ranging from 50 to 100 mg/kg perorally without any symptom of stimulation. Raubasine does not increase the analgetic effects of morphine while tetrahydroalstonine does.

The diphasic aspect of the pharmacological effects produced by tetrahydroalstonine may allow to conclude to a mechanism of action both peripheric and central.

EXAMPLE 3

Pharmaceutical composition incorporating Tetrahydroalstonine:

a. Capsules containing 20 mg tetrahydroalstonine per unit dosage

| | |
|---|---|
| Tetrahydroalstonine | 20 g |
| Lactose | 145 g |
| Magnesium stearate | 5 g |
| for 100 capsules. | |

b. Tablets containing 20 mg Tetrahydroalstonine

| | |
|---|---|
| Tetrahydroalstonine | 20 g |
| Lactose | 55 g |
| Maize starch | 10 g |
| Calcium phosphate | 54 g |
| Hydrolysed starch — sold under the trade name "Primogel" | 5 g |
| Talc | 5 g |
| Magnesium stearate | 1 g |
| for 100 tablets weighing about 0,155 g | |

What we claim is:

1. A method for increasing the peripheral blood flow in capillary and venous circulation in humans or animals which comprises administering to said humans or animals in need of said method an effective amount, for increasing the peripheral blood flow in capillary and venous circulation, of a compound selected from the group consisting of tetrahydroalstonine and an acid addition salt thereof.

2. The method of claim 1 wherein the effective amount ranges from 0.5 to 100 mg/kg daily.

3. The method of claim 1 wherein the effective amount ranges from 0.6 to 60 mg/kg per oral unit dosage.

* * * * *